United States Patent [19]

Green et al.

[11] Patent Number: 5,811,014
[45] Date of Patent: Sep. 22, 1998

[54] HAZARDOUS FLOWABLE WASTE SANITIZING AND REMEDIATING PROCESS AND APPARATUS

[75] Inventors: Lawrence M. Green; Adam M. Werner, both of Miami, Fla.

[73] Assignee: Sanitrol Systems, Inc., Miami, Fla.

[21] Appl. No.: 745,511

[22] Filed: Nov. 12, 1996

[51] Int. Cl.$^6$ ..................................................... C02F 1/32
[52] U.S. Cl. ........................ 210/748; 204/660; 210/760; 210/764; 422/22; 422/24; 422/28
[58] Field of Search ................................. 210/748, 760, 210/764; 422/22, 24, 28; 204/660

[56] References Cited

U.S. PATENT DOCUMENTS

| | | | |
|---|---|---|---|
| 3,788,473 | 1/1974 | King | 210/243 |
| 5,254,229 | 10/1993 | Ohmi et al. | 204/157.15 |
| 5,413,768 | 5/1995 | Stanley, Jr. | 210/748 |
| 5,417,852 | 5/1995 | Furness, Jr. et al. | 210/202 |
| 5,422,068 | 6/1995 | Shalaby et al. | 422/22 |
| 5,457,269 | 10/1995 | Schonberg | 210/748 |
| 5,603,972 | 2/1997 | McFarland | 422/22 |
| 5,679,257 | 10/1997 | Coate et al. | 210/748 |

*Primary Examiner*—Jay H. Woo
*Assistant Examiner*—Betsey J. Morrison
*Attorney, Agent, or Firm*—David L. Garrison; Matthew J. Marquardt

[57] ABSTRACT

A process for treating flowable waste material to sanitize contaminants in the material includes the steps of neutralizing the charges of the molecules of the contaminants in the flowable waste material, for causing the molecules to separate from each other to increase treatment efficiency; exposing the flowable waste material to ozone; exposing the flowable waste material to electron beam radiation; exposing the flowable waste material to ultraviolet radiation; and exposing the flowable waste material to an ozone destructor mechanism. An apparatus is provided for treating and sanitizing flowable waste material containing contaminants, including an allotropic cell having a low density polyethylene sleeve removably secured over the tube outer surface for collecting material deposited onto the tube from the flowable waste material so that the deposited material is removable together with the sleeve. A charge neutralizing module includes a segment of electrically conductive tube through which the flowable waste material is passed; a sacrificial anode member; and lead wires interconnecting the electrically conductive tube and the sacrificial anode member; for neutralizing the charges of molecules of the contaminants for increased treatment efficiency. Charge-carrying fins extend from within the tube radially outwardly, intersecting and extending outwardly beyond the tube to form a charge gathering terminal; where the lead wires are connected to the charge-carrying terminal.

9 Claims, 3 Drawing Sheets

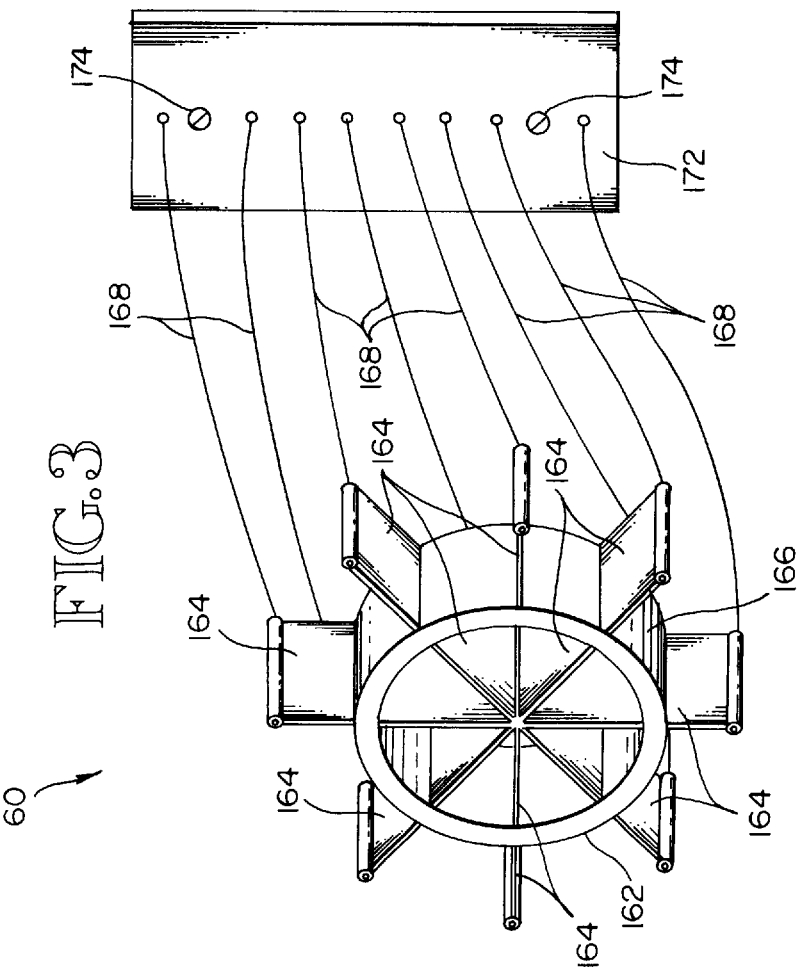
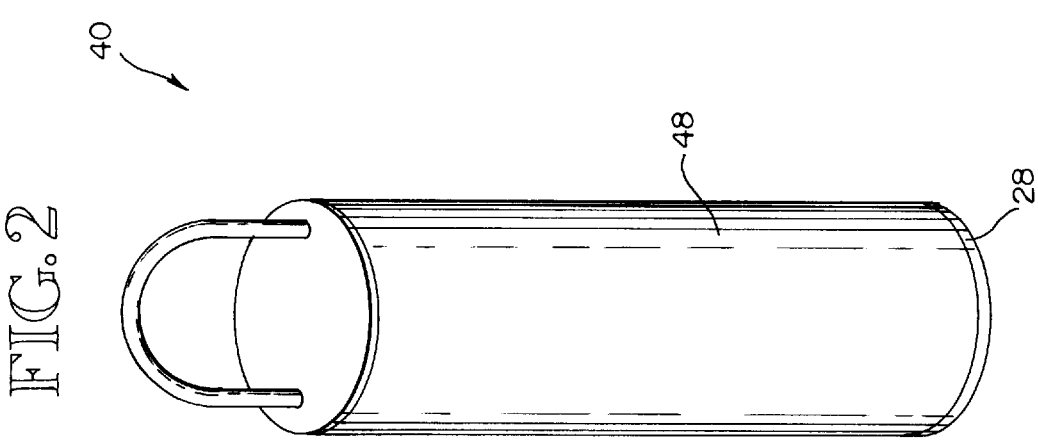

HAZARDOUS FLOWABLE WASTE SANITIZING AND REMEDIATING PROCESS AND APPARATUS

BACKGROUND OF THE INVENTION

1. Field of the Invention

The present invention relates generally to the field of hazardous waste treatment. More specifically the present invention relates to a pre-treatment process of and apparatus for treating dangerous biological waste, waste chemicals and other flowable waste to eliminate or render harmless, or inert, organic waste materials such as diseased human blood, cells and tissue, residual solvents used in cleaning human cells and tissue, and microorganisms for safe, charge neutralized and harborless release into conventional utility sewer systems, septic tanks and holding tanks, while meeting environmental standards established for these specific materials. This process and apparatus aid in achieving compliance with environmental statutes and regulations with maximum efficiency and at minimal cost.

The process includes a critical step of neutralizing the charge of the water molecules and of the contaminant molecules in the water, so that the contaminant molecules separate from each other for efficient treatment and removal. This step is combined with steps of exposing the water to ozone, then once again neutralizing the charge of the water and contaminant molecules, then exposing the water to electron beam radiation (E-Beam), then to ultraviolet UV radiation, and then once again to ozone and to UV radiation, in which the neutralized and separated contaminant molecules are treated efficiently, and finally to first and second exposures to ozone destructor means. Redundant treatment steps are provided for public safety. Should the equipment performing any step fail, the redundant step continues to perform its function until the equipment failure is recognized by automated remote detection.

The apparatus includes a charge neutralizing allotropic cell (A-Cell), which preferably takes the form of a copper tube with magnetite inside it. The A-Cell either supplies charges or removes charges from molecules, as necessary, to render the molecules neutral. Water hardening elements are attracted and attach themselves to the A-Cell surface, forming a deposit layer which lowers the neutralizing efficiency of the A-Cell and inhibits laminar flow around the cell. For this reason, the copper tube is inventively provided with a replaceable film or sleeve of low density polyethylene secured, such as by heat shrinking, to its outer surface. Low density polyethylene is more permeable to a flux lines of a magnetic field than high density polyethylene. The hardening elements cling to the sleeve, and after a certain amount of deposit build-up on the sleeve, the sleeve is removed from the copper tube together with the caked deposits and is replaced with clean sleeve. The sleeve eliminates the need for abrasion cleaning of the tube.

The second device used in the process for charge neutralization is termed an In-line Continuous Electrostatic Electrolysis Destructor/Collector (ICEED) module. The purpose of the ICEED module is to eliminate positive and negative charges imparted to molecules by friction of the water passing through system pipes and by the treatment process itself. This neutralizing function, once again, eliminates the bond between the waste molecules, permitting the waste molecules to separate from each other for efficient treatment.

The ICEED module includes a segment of copper tube through which the water to be treated is passed, the copper tube being externally covered by CPVC or PVC pipe used throughout the system for carrying the flow stream. Charge-carrying fins extend radially outward from the tube longitudinal axis, intersecting and extending beyond the tube side wall to form charge gathering terminals. The terminals are each connected to a lead wire which carries the charges to a zinc receptor plate to which the lead wires are connected. The zinc receptor plate is a sacrificial anode, and is gradually depleted and periodically replaced as the system operates. The receptor plate is fastened to an insulated surface with non-conductive fasteners. Another inventive charge neutralizing module termed an N-Cell module is alternatively provided, as described more fully in the Detailed Description.

Ozone destruction is preferably performed by a charcoal filter. As a redundant mechanism, ozone destruction is performed by an electric resistance heating element contained within an element cover or alternatively by microwave heating. The element and cover extend into the waste stream.

2. Description of the Prior Art

There have long been various methods and devices for sanitizing waste material. Municipal sewer systems traditionally have been used for treatment, removal, and processing of human waste products for various uses, including urine and fecal materials. Private and industrial users, however, have used the municipal sewer systems for disposing of all types of hazardous materials, including chemicals and contaminated organic materials, resulting in dangerous environmental pollution that cannot be handled by conventional sewer systems, municipalities cannot be expected to clean up or in any way remove hazardous pollutants from such discharges. The U.S. Government has begun environmental regulations to prevent the use of sewer systems for the transmission of very hazardous materials.

Hospitals, for example, generate huge quantities of hazardous, contaminated, organic waste materials, such as diseased human blood, diseased human cells, and diseased human tissue, all of which is, and should be, specifically pre-treated under highly controlled environmental conditions to prevent this hazardous waste from being exposed to the public. Other institutions generate dangerous waste products as well. Embalming techniques performed by funeral homes often result in the discharge of waste materials from cadavers into municipal sewer systems. Film processing also often results in the discharge of hazardous chemicals into sewer systems.

Various processes and mechanisms have been proposed to treat hazardous waste materials prior to their introduction into public and private sewer and sewage collection systems. These treatment processes, described below by example, have lacked efficiency and have permitted periodic, inevitable equipment failure to lead to the release of inadequately treated waste materials and thus have endangered the public.

Lund, et al, U.S. Pat. No. 4,028,246, discloses a sewage effluent treatment device. Lund, et al., passes effluent through an ozone contact unit while simultaneously exposing the effluent to ultraviolet light. The effluent then flows through a carbon filter and is exposed to gamma radiation.

Hellman, U.S. Pat. No. 4,687,574, teaches a mobile water treatment device. Hellman includes a holding tank which feeds waste water through a screen to remove gross solids. The waste water is then chemically treated in a flocculator which coagulates or "gathers" solids from the liquid waste water. The flocculator chemically precipitates solids from the waste water. The waste water is then fed into a separator made of very small plates or laminates, to remove the precipitated solids and subsequently aerated with ozone.

Stevens, et al., U.S. Pat. No. 4,793,931, reveals a process for treatment of waste containing solid or liquid phase contaminants. Stevens discloses the process steps of passing contaminated waste through a perfluorinated solvent, a certain chemical such as a hydrophilic solvent, acetone, methanol or water, and then extracting the solvent from the waste. Finally, the remaining waste is aerated with ozone and exposed to UV radiation.

Johnson, et al., U.S. Pat. No. 4,563,286, teaches an allotropic gas water purification system which simultaneously exposes waste water to ozone and to UV radiation. The Johnson system employs a treatment agent, an ionized oxygen allotropic gas in multiple or multivalent ion charge forms.

Agueda, et al., U.S. Pat. No. 5,266,216, reveals a device which purifies water in a domestic water holding tank by bubbling ozone through the water.

Beitzel, U.S. Pat. No. 4,273,660, discloses a waste water purification device. Beitzel exposes the waste water to ozone and UV light, while the waste water is housed in a cylindrical chamber. The chamber contains an elongate tubular UV lamp.

Feather, U.S. Pat. No. 4,414,924, teaches a device for removing hydrogen sulfide and iron from well water. Feather includes an upper chamber which receives untreated water. The upper chamber is connected by dilution flow control orifices to a lower chamber to permit ozone and oxygen from the lower chamber to bubble upward into the upper chamber. The water then passes into the lower chamber where remaining traces of the hydrogen sulfide are removed by bubbling additional ozone through it. Effective ionization is assured by inducing a vortex that rotates the water in the lower chamber. Finally, the water is passed through a magnetic field to improve softness and remove iron. Thomas, Jr. et al., U.S. Pat. No. 4,915,846, discloses a device which precipitates dye particles from waste water with an electric field.

Satoh, U.S. Pat. No. 5,059,332, teaches a device for treating oil sludge and oily waste water. Satoh separates the oil sludge into oil-containing water and oily dust. The oily dust is substantially separated into oil-free dust, which is removed, and water containing oil and metals. Finally, the water is chemically treated to separate the oil.

Satoh, U.S. Pat. No. 5,092,998, reveals an electrolytic cell for treating aqueous solutions by exposure to a strong electromagnetic field.

It is thus an object of the present invention to provide an apparatus and process for treating water containing hazardous waste materials such as viruses, bacteria, human cells and chemical solvents which renders the water safe enough, and in conformance with government regulations for, discharge into a conventional municipal sewer system.

It is another object of the present invention to provide such an apparatus and process which neutralizes the molecular charges of waste materials so that the molecules separate from each other for more efficient treatment.

It is still another object of the present invention to provide such an apparatus and process which includes modules for performing a series of treatment steps including ozone mixing, and exposure to UV and E-Beam radiation.

It is finally an object of the present invention to provide such an apparatus and process which are highly reliable, efficient and economical to respectively operate and perform.

SUMMARY OF THE INVENTION

The present invention accomplishes the above-stated objectives, as well as others, as may be determined by a fair reading and interpretation of the entire specification.

A process is provided for treating flowable hazardous waste material to sanitize contaminants in the material, including the steps of neutralizing the charges of the molecules of the contaminants in the flowable waste material, for causing the molecules to separate from each other to increase treatment efficiency; exposing the flowable waste material to ozone; neutralizing the charges of the molecules of the contaminants; exposing the flowable waste material to electron beam radiation; exposing the flowable waste material to ultraviolet radiation; exposing the flowable waste material to ozone; exposing the flowable waste material to ultraviolet radiation; and exposing the flowable waste material to an ozone destructor mechanisms.

A process is also provided for treating flowable waste material to sanitize contaminants in the material, including the step of neutralizing the charges of the molecules of the contaminants in the flowable waste material, for causing the molecules to separate from each other to increase treatment efficiency.

A process is also provided for treating flowable waste material to sanitize contaminants in the material, including the steps of neutralizing the charges of the molecules of the contaminants in the flowable waste material, for causing the molecules to separate from each other to increase treatment efficiency; exposing the flowable waste material to ozone; exposing the flowable waste material to electron beam radiation; exposing the flowable waste material to ultraviolet radiation; and exposing the flowable waste material to an ozone destructor mechanism.

An apparatus is provided for treating and sanitizing flowable waste material containing contaminants, including a tube having a tube outer surface and containing molecular charge neutralizing substance; a sleeve of sleeve material removably secured over at least part of the tube outer surface for collecting material deposited onto the tube from the flowable waste material so that the deposited material is removable together with the sleeve. The sleeve is preferably formed of low density polyethylene. The sleeve is preferably secured around the tube by heat shrinking onto the tube outer surface. The molecule neutralizing substance optionally includes magnetite.

An apparatus is also provided for treating and sanitizing flowable waste material containing contaminants, including a segment of electrically conductive tube through which the flowable waste material is passed; a sacrificial anode member; and a lead wire interconnecting the electrically conductive tube and the sacrificial anode member; for neutralizing the charges of molecules of the contaminants for increased treatment efficiency.

The apparatus preferably additionally includes a charge-carrying fin extending from within the tube outwardly, intersecting and extending outwardly beyond the tube to form a charge gathering terminal; where the lead wire is connected to the charge-carrying terminal. The sacrificial anode member preferably includes zinc. The segment of tube and the fin are both preferably formed of copper, and an external layer of CPVC or PVC tubing preferably covers the outer copper tube surface.

An apparatus is provided for conditioning flowable matter, including a tubular magnet having a tube inner surface and a tube outer surface for passing the flowable matter. The apparatus preferably additionally includes a sleeve of sleeve material removably secured along at least part of the tube inner surface for collecting material deposited within the tubular magnet from the flowable matter so that the deposited material is removable together with the sleeve.

BRIEF DESCRIPTION OF THE DRAWINGS

Various other objects, advantages, and features of the invention will become apparent to those skilled in the art from the following discussion taken in conjunction with the following drawings, in which:

FIG. 2 is a perspective view of an allotropic cell fitted with the inventive deposit removal sleeve.

FIG. 3 is a perspective view of the inventive In-line Continuous Electrostatic Electrolysis Destructor/Collector (ICEED) module.

DETAILED DESCRIPTION OF THE PREFERRED EMBODIMENTS

Figure 1:
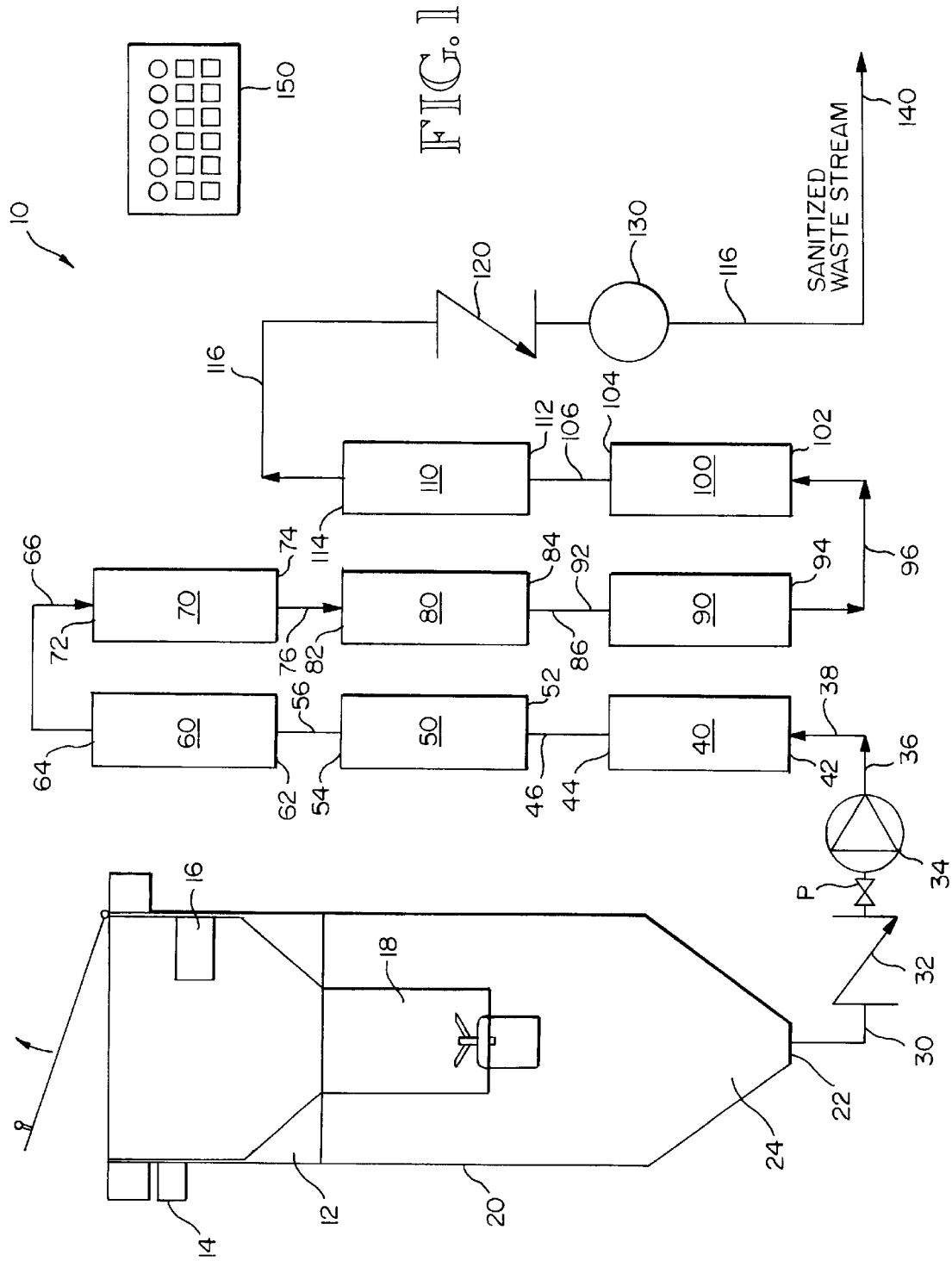
FIG. 1 is a schematic view of the complete waste material treatment system.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

Preferred Process

In practicing the invention, the following process may be used, as indicated generally in FIG. 1. The process preferably includes the initial steps of drawing the flowable waste material, such as water containing contaminants, from a waste source into a chamber and mixing the waste material for uniform treatment. The process further includes the critical step of neutralizing the charge of the contaminant or waste molecules, so that the molecules separate from each other for more efficient treatment. This charge neutralizing step is combined with steps of exposing the water to ozone, then once again neutralizing the charge of the waste material molecules, then exposing the waste material to electron beam (E-Beam) radiation, then to ultraviolet UV radiation, and then once again to ozone and to UV radiation, in which the neutralized and separated waste material molecules are more efficiently treated, and finally to first and second ozone destructor means. An ozone recovery step is therefore not needed. Redundant treatment steps are provided for public safety. Should the equipment performing any step fail, the redundant step continues to perform its function until the equipment failure is recognized by automated remote detection and repaired.

First Preferred Embodiment

Referring to FIGS. 1–4, a system 10 for treating flowable waste materials such as waste water, waste chemicals and flowable biological waste is disclosed. As shown in the schematic diagram of FIG. 1, system 10 preferably includes a waste receiving chamber 12 having at least one inlet 14 and an open top for receiving waste, such as an aspirator gathering waste from a cadaver being dissected. Water together with a waste stream, or water alone, is pumped into receiving chamber 12 through inlet 14 for mixing with solid and semi-solid waste to become flowable through system 10.

A mechanical mixer 18 chops and blends the organic materials in the waste stream into a homogeneous state for uniform presentation to treatment means, to optimize sanitization of the stream. Mixer 18 discharges the mixed waste stream into a retaining tank 20. In the preferred embodiment, tank 20 includes a tank outlet 22 controlled by a float switch 24. When the amount of waste in tank 20 reaches a predetermined volume, float switch 24 activates a valve opening tank outlet 22 and allowing the waste to flow out of tank 20 through waste piping 30. See FIG. 1.

Piping 30 fluidly connects tank outlet 22 with a check valve 32, and check valve 32 with a pump 34. Between check valve 32 and pump 34 is a plug valve P. Pump 34 has a discharge end 36 and delivers the waste stream through additional piping 38 to an allotropic cell (A-Cell) 40 having an inlet end 42 and an outlet end 44. A-Cell 40 is a charge neutralizing device which either supplies charges or removes charges from passing molecules in the waste stream, as necessary, to render the molecules neutral. A-Cell 40 preferably takes the form of a copper tube 28 with magnetite inside it as described in Cervantes, U.S. Pat. No. 5,522,992, issued on Jun. 4, 1996. Alternative A-Cells 40 containing an active material other than magnetite are contemplated. Water hardening molecules are attracted and attach themselves to the A-Cell surface, forming a caked deposit layer which lowers the neutralizing efficiency of the A-Cell 40 and inhibits laminar waste stream flow over and around the A-Cell 40. For this reason, the tube 28 is provided with an inventive replaceable film or sleeve 48 of low density polyethylene secured, such as by heat shrinking, to its outer surface. See FIG. 2. Low density polyethylene is more permeable to the lines of flux of a magnetic field than high density polyethylene. The hardening elements cling to the sleeve 48, and after a certain amount of deposit build-up on the sleeve 48, the sleeve 48 is removed from the tube 28 together with the caked deposits and is replaced with a clean sleeve 48. Sleeve 48 eliminates the need to abrasion clean the tube 28.

The waste stream exits outlet 44 and travels through piping 46 to a first ozone generation module 50 having an inlet end 52 and an outlet end 54. The waste stream enters the first ozone generation module 50, at inlet 52, and is exposed to ozone gas prior to exiting through outlet 54 into piping 56.

The waste stream is carried by piping 56 into a second molecule charge neutralizing device which is termed an In-line Continuous Electrostatic Electrolysis (ICEED) module 60. The purpose of the ICEED module 60 is to eliminate positive and negative charges imparted to molecules by friction of the water passing through system 10 pipes and by the treatment process itself. This neutralizing function once again eliminates the bond between the waste molecules, permitting the waste molecules to separate from each other.

ICEED module 60 is a segment of copper tube 162 through which the waste stream passes, the copper tube being externally covered by CPVC or PVC pipe used throughout system 10 for carrying the flow stream. Radial charge-carrying fins 164 extend from the tube 162 longitudinal axis outwardly, intersecting and extending outwardly beyond the tube side wall 166 to form charge gathering terminals. The terminals are each connected to a lead wire 168 which carries the charges to a zinc receptor plate 172 to which the lead wires 168 are connected. Zinc receptor plate 172 is a sacrificial anode, and is gradually depleted and periodically replaced. Receptor plate 172 is fastened to an insulated surface with non-conductive fasteners 174. It is contemplated that the surfaces of module 60 making contact with the waste stream be covered with a removable film for deposit cleaning purposes, similar in structure and function to the sleeve 48 of A-Cell 40. ICEED module 60 aids in achieving compliance with environmental statutes and regulations with maximum efficiently and at minimal cost.

The waste stream exits module 60 and travels through piping 66 to an electron beam (E-Beam) radiating and exposing module 70. Module 70 preferably includes a cathode ray tube, but alternatively includes an electrostatic accelerator or a pulsed linear induction accelerator.

The waste stream exits E-Beam module 70 outlet end 74 and travels through piping 76 to a UV radiating and exposing device which comprises a UV module 80, preferably a UV radiating germicidal lamp, having an inlet end 82 and an outlet end 84. The waste stream enters the UV module 80 at inlet end 82 and is exposed to UV radiation prior to exiting the module through outlet end 84.

The waste stream exits outlet 84 and travels through piping 86 to a second ozone saturation means which comprises a second ozone generation module 90 having an inlet end 92 and an outlet end 94. The waste stream enters module 90 at inlet end 92, and is combined with ozone prior to exiting module 90 through outlet end 94.

The waste stream exits outlet 94 and travels through piping 96 to a second UV radiating exposing means which comprises a UV module 100 having an inlet end 102 and an outlet end 104. The waste stream enters the second UV module 100, at inlet end 102, and is exposed to a UV radiating germicidal lamp prior to exiting the module through outlet 104.

The waste stream exits outlet end 104 and travels through piping 106 to an ozone destructor/inhibitor means which comprises an ozone destructor module 110 having an inlet end 112 and an outlet end 114.

The waste stream enters the ozone destructor module 110. at inlet end 112, and the ozone in the stream is neutralized or otherwise broken down prior to exiting the module 110 through outlet end 114. Ozone destruction is preferably performed by a charcoal filter and as a redundant step by an electric resistance heating element contained within an element cover. The element and cover extend into the waste stream. Microwave heating means is a preferred alternative to the resistance heating element.

Piping 116 is connected to outlet end 114 and carries the treated stream to a system discharge port 140, where the treated stream is discharged, preferably directly into a conventional sanitary sewer system (not shown). A check valve 120 and vacuum breaker 130 are preferably connected in-line to piping 116. Check valve 120 prevents reverse flow of the treated stream. Vacuum breaker 130 pressure compensates for any venturi effect caused by sewage flowing past the system 10 discharge port 140 through the receiving sanitary sewer system, to prevent a vacuum from forming at the discharge port 140 and accelerating the waste stream through the system 10.

A control means 150 provides for overall system monitoring and control. Control means 150 preferably includes sensors and displays for monitoring such parameters as flow rates, pressures and temperatures, and preferably further provides for automatic actuation of all of the above-referenced valves and pumps. Control means 150 also preferably monitors the operation of the system 10 elements to immediately detect any equipment failure and promptly alert appropriate personell.

Figure 4:
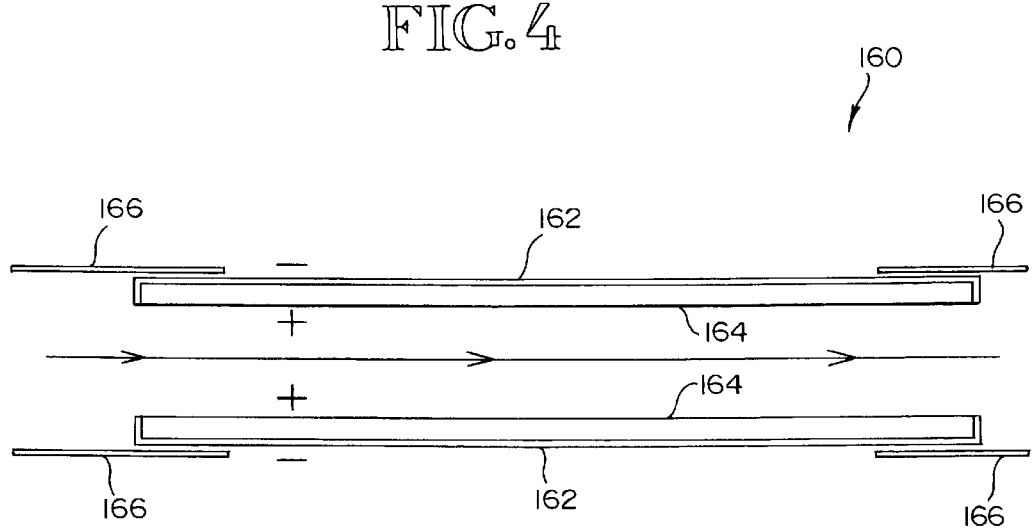
FIG. 4 is a cross-sectional side view of the inventive N-Cell charge neutralizing module.

An alternative to ICEED module 60 is what will be termed an N-Cell extractor tube (N-Cell) module 160, illustrated in FIG. 4. N-Cell module 160 includes a tubular magnet 162 which receives and passes the waste stream, for neutralizing the charges of molecules within the waste stream passing through tubular magnet 162. The inner surface of tubular magnet 162 preferably has a positive charge and the exterior surface has a negative charge, as shown, An internal sleeve 164 of low density polyethylene film, preferably of one to three mils thickness. Sleeve 164 is removably secured along the interior surface of tubular magnet 162, such as by wrapping the ends of sleeve 164 over and around the outside surface at each end of tubular magnet 162 and heat shrinking these sleeve 164 ends onto the tubular magnet 162 outer surface. The ends of tubular magnet 162 and of sleeve 164 are preferably snugly fitted into ends of CPV or PVC pipe 166 forming a line within system 10. The ICEED module 60 and N-Cell module 160 may also be used to condition water which does not contain harmful contaminants by neutralizing any charges in the water.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim as our invention:

1. A process for treating flowable material to sanitize the material, comprising the steps of:

neutralizing the charges of the molecules of said contaminants in said flowable material, for causing said molecules to separate from each other to increase treatment efficiency;

exposing said flowable material to ozone;

neutralizing the charges of said molecules of said contaminants by passing said material through a tubular magnet, said tubular magnet having positive charge on the interior thereof and a negative charge on the exterior thereof;

exposing said flowable material to electron beam radiation;

exposing said flowable material to ultraviolet radiation;

exposing said flowable material to ozone;

exposing said flowable material to ultraviolet radiation;

and exposing said flowable material to ozone destructor means.

2. The method of claim 1 wherein said tubular magnet further comprises a removable sleeve of low density polyethylene on the exposed surface thereof and said process including the further step of periodically removing and replacing said sleeve.

3. The method of claim 2 wherein said removable sleeve is a heat shrinkable low density polyethylene film.

4. The method of claim 2 further including the steps of inserting said sleeve into the inside of said tubular magnet, wrapping the ends of sleeve over and around the outside surface at each end of the tubular magnet, and heat shrinking the sleeve ends onto the tubular magnet outer surface.

5. A process for treating flowable material to sanitize the material, comprising the steps of:

mixing said flowable material into a homogeneous state;

neutralizing the charges of the molecules of said contaminants in said flowable material by passing said material through a copper pipe having an active material therein, to render said molecules neutral to separate from each other to increase treatment efficiency;

exposing said flowable material to ozone;

exposing said flowable material to electron beam radiation;

exposing said flowable material to ultraviolet radiation;

and exposing said flowable material to ozone destructor means.

6. The method of claim 5 wherein said tubular magnet further comprises a removable sleeve of low density polyethylene on the exposed surface thereof and said process including the further step of periodically removing and replacing said sleeve.

7. The method of claim 6 wherein said removable sleeve is a heat shrinkable low density polyethylene film.

8. The method of claim 6 further including the steps of inserting said sleeve into the inside of said tubular magnet, wrapping the ends of sleeve over and around the outside surface at each end of the tubular magnet, and heat shrinking the sleeve ends onto the tubular magnet outer surface.

9. The method of claim 5 wherein said active material is magnetic.

* * * * *